United States Patent
Kumar et al.

(10) Patent No.: US 6,939,972 B2
(45) Date of Patent: Sep. 6, 2005

(54) PROCESS FOR PRODUCING 4-DIMETHYL AMINO PYRIDINE (4-DMAP)

(75) Inventors: Mahendra Kumar, Gajraula (IN); Shailendra Kumar Singh, Gajraula (IN); Ashutosh Agarwal, Gajraula (IN)

(73) Assignee: M/s. Jubilant Organosys Limited, Noida (IN)

( * ) Notice: Subject to any disclaimer, the term of this patent is extended or adjusted under 35 U.S.C. 154(b) by 0 days.

(21) Appl. No.: 10/407,773

(22) Filed: Apr. 4, 2003

(65) Prior Publication Data

US 2004/0106801 A1 Jun. 3, 2004

(30) Foreign Application Priority Data

Nov. 28, 2002 (IN) .................................. 1197/DEL/2002

(51) Int. Cl.[7] ............................................ C07D 213/02
(52) U.S. Cl. ...................................................... 546/304
(58) Field of Search .......................................... 546/304

(56) References Cited

U.S. PATENT DOCUMENTS

| 4,158,093 A | 6/1979 | Bailey et al. |
| 4,220,785 A | 9/1980 | Oude Alink et al. |
| 4,672,121 A | 6/1987 | Nummy et al. |
| 4,772,713 A | 9/1988 | Nummy et al. |

OTHER PUBLICATIONS

Qing, Li Bao, Research work on synthesis of highly effective acidylation catalytic agent—4–di–methyl amino pyridine, Department of Chemical Industry, Costume Academy, Beijing 100029, 2001 T CH 58, pp. 1–18.

Gen, Xi Guan, et al., Improvement in the method of synthesis of 4–di–methyl amino pyriding, Chemical Reagent, 1998, 20(2), 119–120, 2001 T CH 59.

Primary Examiner—Zinna Northington Davis
(74) Attorney, Agent, or Firm—Christie, Parker & Hale, LLP

(57) ABSTRACT

An improved process for producing 4-dimethyl amino pyridine is provided. The process comprises quaternizing pyridine with a suitable quaternizing agent in the presence of organic solvent, isolating the resulting salt and aminating the salt, N-[4-pyridyl] pyridinium chloride hydrochloride, with N,N-dimethyl formamide. The resultant reaction mass is hydrolysed in the presence of a base, extracted with an aromatic solvent and distilled under vacuum to produce 4-dimethyl amino pyridine.

9 Claims, No Drawings

PROCESS FOR PRODUCING 4-DIMETHYL AMINO PYRIDINE (4-DMAP)

CROSS REFERENCE TO RELATED APPLICATION

This application claims priority to Indian Application No. 1197/DEL/2002, filed Nov. 28, 2002, the disclosure of which is incorporated herein by reference.

FIELD OF THE INVENTION

This invention generally relates to a process for producing 4-dimethyl amino pyridine (4-DMAP), and more particularly, to an improved process for producing large quantities of 4-dimethyl amino pyridine (4-DMAP).

BACKGROUND OF THE INVENTION

4-Dimethyl amino pyridine ($C_7H_{10}N_2$) belongs to the category of 4-position substitution derivatives of pyridine. It is widely used as a hypernucleophilic acylation catalyst. 4-Dimethyl amino pyridine is a highly efficient catalyst for acylation reactions as compared to other traditional acylation catalytic agents due to its effectiveness, cost efficiency and long time efficiency property.

Several processes are known for the preparation of 4-dimethyl amino pyridine. The known processes differ from each other with respect to the different chemical processes employed.

U.S. Pat. No. 4,220,785 to Oude Alink, et al. discloses the preparation of substituted pyridines by reacting aldehydes, amines, and lower carboxylic acids, such as acetic acid, in the presence of oxygen. The N-substituted pyridinium salts formed are then converted to pyridines by thermal dealkylation.

U.S. Pat. No. 4,158,093 to Baily et al. discloses a process in which a 4-substituted pyridine base is first quaternized with 2-vinyl pyridine in the presence of a strong acid to give a pyridyl ethyl quaternery salt. This activated quaternery salt is subjected to nucleophilic substitution at the 4-position and then dequaternized in the presence of sodium hydroxide.

U.S. Pat. No. 4,672,121 and U.S. Pat. No. 4,772,713 to Nummy et al. disclose a process for preparing a 4-substituted pyridine product from a starting pyridine substituted in the 4-position by a leaving group susceptible to nucleophilic displacement when the starting pyridine is quaternized. The process comprises quaternizing the starting pyridine, with acrylamide, N-monoalkylacrylamide or N-dialkylacrylamide under effective acidic conditions; subjecting the resultant, corresponding quaternized starting pyridine to a nucleophilic displacement reaction with a reagent that reacts to produce the corresponding 4-substituted pyridine; and dequaternizing the latter under effective basic conditions to liberate the desired 4substituted pyridine product.

An article authored by Xi Guan Gen et al. published in Chemical Reagent, 1998, 20(2), 119-120, discloses a process, in which pyridine is quaternized with thionyl chloride ($SOCl_2$) in the presence of ethyl acetate, and then aminating the resulting salt, N-[4-pyridyl]pyridinium chloride hydrochloride, with N,N-dimethyl formamide. The resulting reaction mass is hydrolysed in the presence of a base, and extracted with chloroform. This is an improved process compared to the one disclosed in the Chinese article authored by Li Bao Qing, the Department of Chemical Industry, Costume Academy, Beijing 100029.

A significant problem in the above-described processes is that of the formation of highly hazardous and unsafe by-products like hydrogen cyanide and sodium cyanide, which are very unsafe to handle in the laboratory as well as in a commercial-scale manufacturing process. Also, costlier raw materials like cyanopyridine and vinyl pyridine were used in the processes.

Most of these problems have been well addressed by Xi Guan Gen et al. However, the processing of the reaction mass involves many undesirable steps. Also the product quality and yield are not found to be satisfactory, so the process was not found suitable for industrial applications.

Therefore there is a need for an improved process for producing 4-dimethyl amino pyridine especially suitable for large-scale manufacture. Large-scale manufacturing requires the production of the compound in a cost efficient manner, resulting in a need for an improved process for producing 4-dimethyl amino pyridine with high purity and with a better yield.

Another concern with respect to the present invention is to provide a process for producing 4-DMAP where little or no hazardous byproducts are formed so that the process is suitable for industrial use. Also, the known methods do not address the ability to recover and recycle the byproducts.

Known processes are not techno-economically viable. The product quality/yield could be higher, thus making the processes unviable for industrial application. It is therefore desirable to develop a suitable process to address the above-mentioned problems in the known process.

SUMMARY OF THE INVENTION

The present invention is directed to an improved process for the preparation of 4-dimethyl amino pyridine, the process being devised to produce high yields and quality products. The present inventive addresses the disadvantages and complications associated with the processes heretofore disclosed.

In one embodiment the invention provides an improved process for the manufacture of 4-dimethyl amino pyridine comprising first quaternizing pyridine with a suitable quaternizing agent, such as thionyl chloride, in presence of an organic solvent, such as ethyl acetate, and then aminating the resulting salt, such as N-[4-pyridyl]pyridinium chloride hydrochloride, with a suitable aminating agent, such as N,N-dimethyl formamide. The resulting reaction mass is hydrolysed in the presence of a base, extracted with an aromatic solvent, such as benzene, and distilled under vacuum, employing a fractionating column, to give 4-dimethyl amino pyridine with excellent quality and yield.

In another aspect, the present invention is directed to an improved process for producing 4-dimethyl amino pyridine that provides for the recovery of ethyl acetate during salt formation and recycling the ethyl acetate. The process comprises quaternizing pyridine with thionyl chloride in presence of recovered ethyl acetate to provide N-[4-pyridyl]pyridinium chloride hydrochloride and then aminating the resulting salt with N,N-dimethyl formamide. The resulting reaction mass is hydrolysed in presence of a base, extracted with an aromatic solvent, such as benzene, and distilled under vacuum employing a fractionating column to give 4-dimethyl amino pyridine with the desired quality and yield.

In still another aspect of the present invention, an improved process for producing 4-dimethyl amino pyridine is provided. The process comprises refluxing N-[4-pyridyl] pyridinium chloride hydrochloride with N,N-dimethyl formamide for 2 to 3 hrs. After completion of the reaction, pyridine is distilled off. The resultant reaction mass is hydrolysed in the presence of a base and extracted with benzene. The reaction mass thus obtained upon extraction is distilled under vacuum, employing a fractionating column, to get the desired results, i.e., high yield with high quality.

DETAILED DESCRIPTION OF THE INVENTION

The disclosed embodiment of the present invention deals with a process for the preparation of 4-DMAP that has advantages over prior art processes in that it avoids formation of hazardous byproducts, effectively recycles raw materials, uses industrially suitable solvents, and eliminates undesired processing steps to make it comparatively safe and more cost effective.

The major raw materials, namely pyridine and thionyl chloride, and organic solvents such as ethyl acetate, ethyl alcohol and aromatic solvents like benzene, are well known compounds and are easily available.

In one embodiment of the present invention, a process for producing 4-dimethyl amino pyridine is provided. The process comprises initially charging ethyl acetate and pyridine, one by one, under agitation, and maintaining the pot temperature at 25±5° C. Thionyl chloride is then charged gradually while maintaining the temperature below 35° C. After the addition, the reaction mass is refluxed for 4 hours at 77–80° C. After refluxing, the ethyl acetate and unreacted thionyl chloride are distilled off at atmospheric pressure. Finally, mild vacuum (400 to 600 mm Hg) is applied to ensure maximum recovery of ethyl acetate and thionyl chloride. Left over reaction mass is cooled to 40° C. Then anhydrous ethyl alcohol is added slowly while maintaining the temperature below 60° C. The resulting reaction mass is stirred well, then cooled up to 10° C. and then filtered, washed with anhydrous ethyl alcohol and dried under vacuum to get the desired salt N-[4-pyridyl] pyridinium chloride hydrochloride. Mother liquor obtained after filtration is first atmospherically distilled to recover ethyl alcohol and then hydrolysed with caustic lye solution, followed by extraction with benzene and then fractional distillation to recover benzene and pyridine, which can be recycled back into the process.

In another embodiment of the present invention, in the process described above, the obtained salt N-[4-pyridyl] pyridinium chloride hydrochloride is aminated with N,N-dimethyl formamide. The process comprises charging N-[4-pyridyl] pyridinium chloride hydrochloride salt and N,N-dimethyl formamide one by one. The reaction mass is slowly heated to raise the temperature 50 to 60° C. The agitator is started, and the reaction mass is further heated slowly to a reflux temperature of 140 to 150° C. Reflux is continued for 2 hours at 150 to 155° C. After 2 hours of refluxing, the reaction mass is distilled first atmospherically and then under vacuum to recover pyridine to the maximum possible extent. The reaction mass is cooled up to 40° C. and then hydrolysed by adding 10% caustic lye solution, while maintaining the pH at 11 to 12. The neutralised reaction mass is further cooled to 20° C., and the precipitated inorganic cake is filtered off. The mother liquor is extracted with benzene in multiple steps to ensure almost complete extraction. The extracted reaction mass is distilled atmospherically and then under vacuum to recover benzene. The crude 4-DMAP left in the pot is distilled under high vacuum employing a fractionating column to get white to off-white crystals of 4-DMAP in high yield and purity.

The present invention is further illustrated below with reference to the following examples.

EXAMPLE 1

Preparation of N-[4-Pyridyl]pyridinium Chloride Hydrochloride

Ethyl acetate (1127.5 g) and pyridine (807.0 g) were charged in a 5 liter round-bottom flask fitted with a thermowell and double surface condenser. To this was gradually added thionyl chloride (1019.37 g) while maintaining the temperature at 25±5° C. The reaction mass was slowly heated to reflux temperature (77–80° C.), and refluxing was maintained for 4 hours. After the reaction, ethyl acetate and unreacted thionyl chloride were distilled off. Anhydrous ethyl alcohol (1000 ml) was added to the left over mass at 40 to 60° C. Vigorous stirring was performed until a yellow-brown solid was precipitated out after cooling to 10 to 20° C. The precipitated mass was filtered and washed with ethyl alcohol. Wet salt was dried at 60 to 70° C. under vacuum to get N-4[pyridyl] pyridinium chloride hydrochloride (636.0 g, assay 96.5%(acidimetry), yield 52.50% based on pyridine charged). Mother liquor was distilled to recover ethyl alcohol, which can be recycled back into the process. The leftover mass was hydrolysed with dilute caustic lye solution and then extracted with benzene. The extracted mass was fractionally distilled to recover benzene and pyridine, which can be recycled back in the process.

EXAMPLE 2

Preparation of N-[4-Pyridyl]pyridinium Chloride Hydrochloride by Using Recovered Raw Materials Recovered ethyl acetate (1127.5 g) and recovered pyridine (807.0 g) were charged in a 5 liter round bottom flask fitted with a thermowell and double surface condenser. To this was gradually added thionyl chloride (1019.37 g), while maintaining the temperature at 25±5° C. The reaction mass was slowly heated to reflux temperature (77 to 80° C.), and refluxing was maintained for 4 hours. After the reaction, ethyl acetate and unreacted thionyl chloride were distilled off. Anhydrous ethyl alcohol (1000 ml) was added to the left over mass at 40 to 60° C. Vigorous stirring was performed until a yellow-brown solid was precipitated out after cooling to 10 to 20° C. The precipitated mass was filtered and washed with ethyl alcohol. The wet salt was dried at 60–70° C. under vacuum to get N-4[pyridyl] pyridinium chloride hydrochloride (641.0 gm, assay 94.99%, yield 52.1%). The mother liquor was distilled to recover ethyl alcohol, which can be recycled back into the process. The leftover mass was hydrolysed with dilute caustic lye solution and then extracted with benzene. The extracted mass was fractionally distilled to recover benzene and pyridine, which can be recycled back into the process.

EXAMPLE 3

Dequaternization of N-[4-Pyridyl]pyridinium Chloride Hydrochloride

N-[4-Pyridyl] pyridinium chloride hydrochloride (641.0 gm, 94.99% assay, 2.657 mole) and N,N-dimethyl formamide (421 gm, 99% assay, 5.709 mole) were charged in a 2 liter round bottom flask fitted with a stirrer, thermometer pocket and double surface condenser. The reaction mass was slowly heated to reflux temperature (150 to 155° C.), and refluxing continued for 2 to 3 hours. After the completion of the reaction, pyridine was distilled off. The reaction mass was hydrolysed with 10% caustic lye solution (approx. 2846 ml) to maintain the pH at 10 to 12. The hydrolysed mass was cooled to 20° C. and then filtered to get a clear aqueous mother liquor (3540.0 gm). The mother liquor was extracted with benzene (1770 g×1 and 885 g×3). The aqueous phase was discarded. The total organic extracts were taken for benzene recovery. After benzene recovery (4181.6 gm, 94.5% recovery), 4-DMAP was distilled under vacuum employing a fractionating column. 4-DMAP, 211.5 g, 65.05 mole % yield, (based on net double pyridine salt charged) and 99.85% assay by gas chromotography was obtained.

EXAMPLE 4 (COMPARATIVE)

Preparation of 4-Dimethyl Amino Pyridine by Using Chloroform for Extraction

N-[4-Pyridyl] pyridinium chloride hydrochloride (641.0 gm, 94.99% assay, 2.657 mole) and N,N-dimethyl formamide (421 gm, 99% assay, 5.709 mole) were charged in a 2 liter round bottom flask fitted with a stirrer, thermometer pocket and double surface condenser. The reaction mass was slowly heated to reflux temperature (150 to 155° C.), and refluxing continued for 2 to 3 hours. After the completion of the reaction, pyridine was distilled off. The aqueous mother liquor obtained after alkaline hydrolysis and filtration was extracted with chloroform (2940 g×1 and 1470 g×3). A lot of emulsion was observed after extraction, which creates problems with layer separation. The total organic phase was taken for chloroform recovery. After chloroform recovery (6394.5 gm, 87.0% recovery), 4-DMAP was distilled under vacuum employing a fractionating column. 4-DMAP, 208.5 g, 63.83 mole % yield based on net double pyridine salt charged and 99.38% assay was achieved. The chloroform recovery was reduced compared to the recovery of benzene.

EXAMPLE 5 (COMPARATIVE)

Preparation of 4-Dimethyl Amino Pyridine

N-[4-Pyridyl] pyridinium chloride hydrochloride (641.0 gm, 94.99% assay, 2.657 mole) and N,N-dimethyl formamide (421 gm, 99% assay, 5.709 mole) were charged in a 2 liter round bottom flask fitted with a stirrer, thermometer pocket and double surface condenser. The reaction mass was slowly heated to reflux temperature (150 to 155° C.), and refluxing continued for 2 to 3 hours. After the completion of the reaction, pyridine was distilled off. The aqueous mother liquor obtained after alkaline hydrolysis and filtration was extracted with chloroform (2940 g×1 and 1470 g×3). A lot of emulsion was observed after extraction, which creates problem in layer separation. After extraction with chloroform, the organic phase was separated out and treated with charcoal for removing off-color impurities. Light yellow mother liquor was taken for chloroform recovery. After chloroform recovery, 700.0 gm ethyl acetate was added for the crystallization of crude 4-DMAP. After cooling to 0° C. followed by filtration, 180 g 4-DMAP, with 98.97% assay by G.C, and 54.88% yield were recovered. This clearly indicates that in spite of additional steps involved, yield and assay of the 4-DMAP is reduced compared to the process of the present invention.

Certain modifications and improvements of the disclosed invention will occur to those skilled in the art without departing from the scope of invention, which is limited only by the appended claims.

We claim:

1. A process for producing 4-dimethyl amino pyridine comprising:

quaternizing pyridine using a quaternizing agent in the presence of an organic solvent to form a salt;

isolating the salt;

aminating the salt employing an aminating agent to produce an organic mass; extracting the organic mass using an aromatic solvent; and distilling the extracted organic mass to produce 4-dimethyl amino pyridine.

2. The process according to claim 1 wherein the quaternizing agent is thionyl chloride.

3. The process according to claim 1 wherein the organic solvent is ethyl acetate.

4. The process according to claim 3 further comprising recovering ethyl acetate by distillation.

5. The process according to claim 1 wherein the salt formed is N-4-[pyridyl] pyridinium chloride hydrochloride.

6. The process according to claim 1 wherein the aminating agent is N,N-dimethyl formamide.

7. The process according to claim 1 further comprising recovering unreacted pyridine from mother liquor obtained during isolation of the salt.

8. The process according to claim 1 further comprising recovering recycleable pyridine after amination of the salt.

9. The process according to claim 1, wherein the extracted organic mass is distilled using a fractionating column.

\* \* \* \* \*